United States Patent [19]
Chen et al.

[11] Patent Number: 5,837,379
[45] Date of Patent: Nov. 17, 1998

[54] ONCE DAILY PHARMACEUTICAL TABLET HAVING A UNITARY CORE

[75] Inventors: Chih-Ming Chen, Davie; Joseph C. H. Chou, Coral Spring, both of Fla.

[73] Assignee: Andrx Pharmaceuticals, Inc., Fort Lauderdale, Fla.

[21] Appl. No.: 791,999

[22] Filed: Jan. 31, 1997

[51] Int. Cl.$^6$ ............................................. A61K 9/20
[52] U.S. Cl. ..................... 424/465; 424/489; 424/482; 424/480; 424/494; 424/473
[58] Field of Search ................................. 424/465, 490, 424/489, 467, 469, 473

[56] References Cited

U.S. PATENT DOCUMENTS

| | | | |
|---|---|---|---|
| 4,327,725 | 5/1982 | Cortese et al. | 128/260 |
| 4,412,986 | 11/1983 | Kawata et al. | 424/80 |
| 4,503,030 | 3/1985 | Edgren et al. | 424/15 |
| 4,562,069 | 12/1985 | Hegasy et al. | 424/80 |
| 4,587,117 | 5/1986 | Edgren et al. | 424/15 |
| 4,612,008 | 9/1986 | Wong et al. | 604/892 |
| 4,615,698 | 10/1986 | Guittard et al. | 604/892 |
| 4,765,989 | 8/1988 | Wong et al. | 424/473 |
| 4,765,990 | 8/1988 | Sugimoto et al. | 424/438 |
| 4,783,337 | 11/1988 | Wong et al. | 424/468 |
| 4,792,448 | 12/1988 | Ranade | 424/458 |
| 4,808,413 | 2/1989 | Joshi et al. | 424/461 |
| 4,867,985 | 9/1989 | Heafield et al. | 424/78 |
| 4,880,623 | 11/1989 | Piergiorgio et al. | 424/80 |
| 4,882,144 | 11/1989 | Hegasy | 424/80 |
| 4,892,730 | 1/1990 | Hegasy | 424/80 |
| 4,892,741 | 1/1990 | Ohm et al. | 424/479 |
| 4,952,402 | 8/1990 | Sparks et al. | 424/419 |
| 4,966,772 | 10/1990 | Ohm et al. | 424/482 |
| 4,973,469 | 11/1990 | Mulligan et al. | 424/461 |
| 4,981,683 | 1/1991 | Hegasy | 424/80 |
| 5,007,790 | 4/1991 | Shell | 424/451 |
| 5,015,479 | 5/1991 | Mulligan et al. | 424/457 |
| 5,051,263 | 9/1991 | Barry et al. | 424/490 |
| 5,055,306 | 10/1991 | Barry et al. | 424/482 |
| 5,071,642 | 12/1991 | Lahr et al. | 424/474 |
| 5,108,757 | 4/1992 | Erdos et al. | 424/451 |
| 5,128,142 | 7/1992 | Mulligan et al. | 424/457 |
| 5,145,683 | 9/1992 | Rhodes | 424/451 |
| 5,160,734 | 11/1992 | Ganesan et al. | 424/78.38 |
| 5,190,765 | 3/1993 | Jao et al. | 424/473 |
| 5,204,121 | 4/1993 | Bücheler et al. | 424/495 |
| 5,208,037 | 5/1993 | Wright et al. | 424/473 |
| 5,264,446 | 11/1993 | Hegasy et al. | 514/356 |
| 5,266,581 | 11/1993 | Schmidt et al. | 514/356 |
| 5,283,065 | 2/1994 | Doyon et al. | 424/467 |
| 5,326,571 | 7/1994 | Wright et al. | 424/473 |
| 5,395,628 | 3/1995 | Noda et al. | 424/490 |
| 5,430,021 | 7/1995 | Rudnic et al. | 514/14 |
| 5,439,687 | 8/1995 | Compassi | 424/468 |
| 5,447,729 | 9/1995 | Belenduik et al. | 424/490 |
| 5,470,584 | 11/1995 | Hendrickson et al. | 424/490 |
| 5,543,099 | 8/1996 | Zhang et al. | 264/115 |
| 5,543,154 | 8/1996 | Rork et al. | 424/473 |
| 5,543,155 | 8/1996 | Fekete et al. | 424/473 |
| 5,582,838 | 12/1996 | Rork et al. | 424/472 |
| 5,594,013 | 1/1997 | Trigger | 514/356 |

FOREIGN PATENT DOCUMENTS 1456618  11/1976  United Kingdom .

OTHER PUBLICATIONS

Isao Sugimoto et al., "Dissolution and Absorption of Nifedipine From Nifedipine–Polyvinylpyrrolidone Coprecipitate", Drug Development and Industrial Pharmacy, 6(2), 137–160 (1980).

*Primary Examiner*—Thurman K. Page
*Assistant Examiner*—William E. Benston, Jr.
*Attorney, Agent, or Firm*—Hedman, Gibson, & Costigan

[57] ABSTRACT

A controlled release nifedipine tablet which comprises:
(a) a homogeneous compressed core which comprises:
  (i) a medicament;
  (ii) a water soluble osmotic compound
  (iii) one or more osmotic polymers; and
(b) a membrane coating which completely covers said core tablet which comprises a mixture of:
  (i) a water insoluble pharmaceutically acceptable polymer; and
  (ii) an enteric polymer.

15 Claims, 2 Drawing Sheets

ONCE DAILY PHARMACEUTICAL TABLET HAVING A UNITARY CORE

BACKGROUND OF THE INVENTION

The present invention relates to controlled release unit dose formulations of pharmaceuticals. In the prior art, many techniques have been used to provide controlled and extended-release pharmaceutical dosage forms in order to maintain therapeutic serum levels of medicaments and to minimize the effects of missed doses of drugs caused by a lack of patient compliance.

In the prior art, extended release tablets containing osmotic tablets have been described and manufactured which have had an osmotically active drug core surrounded by a semipermeable membrane. The core is divided into two layers (compositions) one of which contains the active drug and the other contains a push layer of pharmacologically inactive ingredients which are osmotically active in the presence of gastrointestinal fluids. An outer water permeable coating covers the tablet which is provided with an aperture that is formed by laser drilling an orifice to allow the drug to be pushed out of the tablet. A product of this type is disclosed in U.S. Pat. No. 4,783,337; 4,765,989; 4,612,008; and 4,327,725 and is sold commercially as Procardia XL®. Other controlled release compositions include those described in U.S. Pat. No. 3,948,254 and U.S. Pat. No. 4,036,227.

The osmotic dosage forms that are disclosed in U.S. Pat. No. 4,783,337 are described as having a passageway which includes an aperture, orifice, hole, porous element, hollow fiber, capillary tube, microporous insert, pore, microporous overlay or bore which extends through the semipermeable lamina wall into a drug layer. The patent also states that the passageway may be formed by mechanical drilling, laser drilling, eroding and erodible element, extracting, dissolving, bursting or leaching a passageway-former from the wall of the osmotic dosage form (col. 14, line 35 et seq.) which are pre-formed in the tablet during the manufacturing process. The only exemplified technique of forming a passageway in U.S. Pat. No. 4,783,337 is the use of a laser to drill a hole in the outer layer of the tablet and the dosage forms are all based on a drug layer superimposed on a secondary layer.

U.S. Pat. No. 4,285,987 described an osmotic tablet which had a laser drilled aperture into the core of the tablet. The laser drilled hole was plugged with leachable sorbitol which was leached out in the presence of gastrointestinal fluid.

U.S. Pat. No. 4,503,030 discloses an osmotic device for delivering drugs to the stomach and the intestine. This device has a shaped wall placed around a compartment which is described as a compartment which maintains its physical and chemical integrity in the stomach but loses its chemical and physical integrity in the intestine. U.S. Pat. No. 4,587,117 describes an oral osmotic device which has a shaped wall which loses its integrity at a pH of 3.5 to 8.0, a compartment and a passageway from the compartment to the exterior of the medical device.

The present invention is concerned with providing an osmotic tablet that avoids the need to have a separate "push" layer in the core which contains no medicament and which avoids the need to have a pre-formed passageway in the tablet to allow the drug to be pushed out of the core.

SUMMARY OF THE INVENTION

The present invention is directed to a controlled release dosage form which comprises:

(a) a homogeneous compressed core which comprises:
 (i) a medicament;
 (ii) a water soluble osmotic compound
 (iii) one or more osmotic polymers; and
(b) a membrane coating which completely covers said core tablet which comprises a mixture of a:
 (i) a water insoluble pharmaceutically acceptable polymer; and
 (ii) an enteric polymer.

It is an object of the invention to provide a controlled release pharmaceutical tablet which has an osmotic core covered with an external polymer membrane that provides therapeutic blood levels of a medicament with once a day administration.

It is also an object of the invention to provide an osmotic tablet which has a homogeneous core composition.

It is also an object of the present invention to provide a controlled release pharmaceutical tablet that has a homogeneous osmotic core and no pre-formed aperture in the external polymeric membrane.

It is also an object of this invention to provide a controlled release pharmaceutical tablet having only a homogeneous osmotic core wherein the osmotic core component may be made using ordinary tablet compression techniques.

These and other objects of the invention will become apparent from the appended specification.

DETAILED DESCRIPTION OF THE INVENTION

Figure 1:
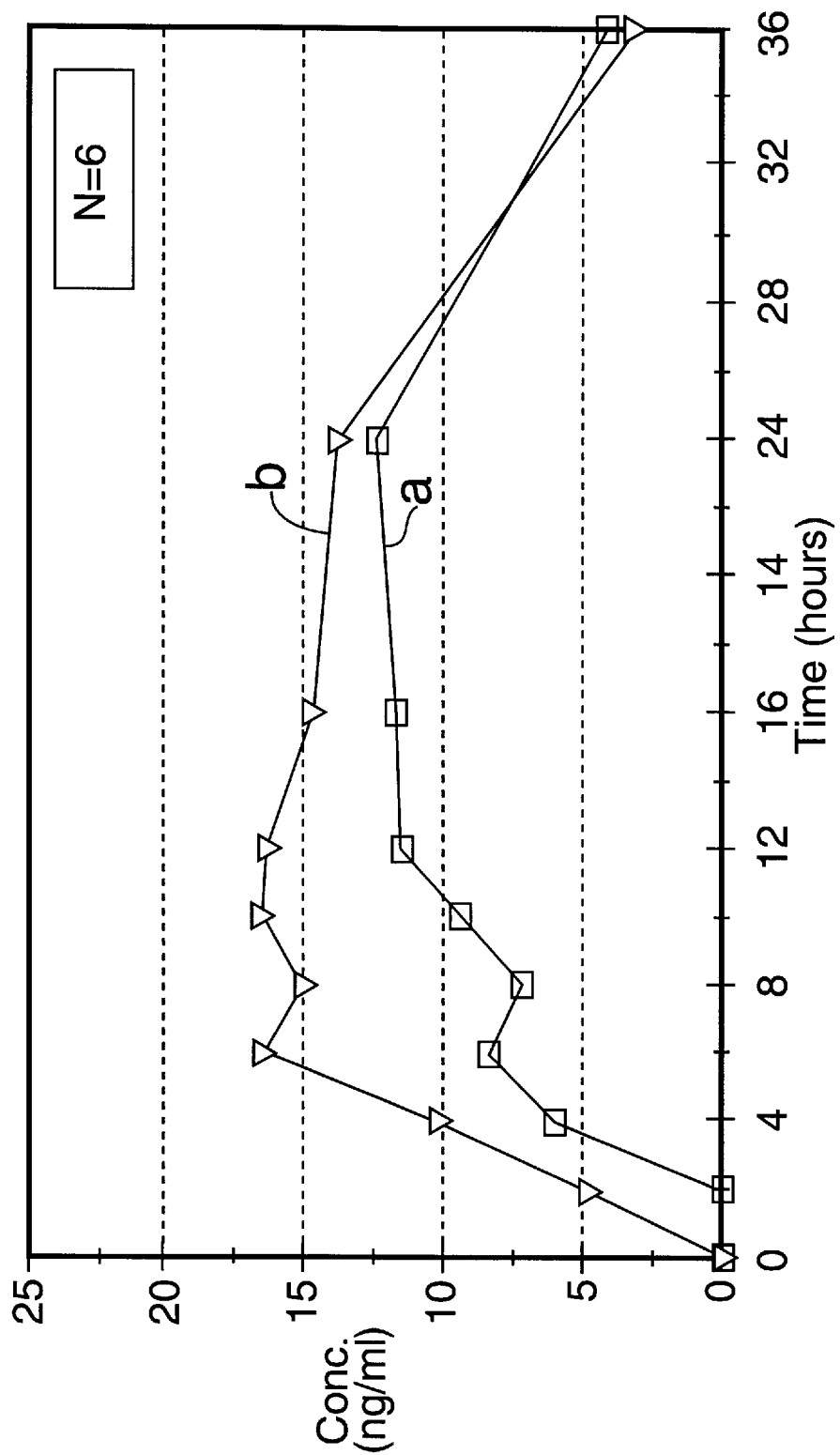
FIG. 1 is a graph which compares the mean plasma concentration of Procardia XL® (a) and a nifedipine tablet (b) prepared according to Example 1 of the present invention in a crossover study involving 6 fasting human volunteers.

Various medicaments may be administered using the osmotic tablet of the present invention. These medicaments include medicaments which are water soluble to practically insoluble in water. The term practically insoluble is used to include those substances which are soluble at a level of 1 part of solute to from 100 to more than 10,000 parts of water per part of solute. The term water soluble includes those substances which are soluble at level of one part of solute to 5 parts of water or less.

Examples of categories of water insoluble medicaments which may be utilized, at therapeutic dose levels, in the controlled release tablets of the invention include antihypertensives, calcium channel blockers, analgesics, antineoplastic agents, anti-microbials, anti-malarials, non-steroidal anti-inflammatory agents, diuretics, anti-arrythmia agents, hypoglycemic agents and the like. Specific examples of medicaments include nifedipine, nisoldipine, nicardipine, nilvadipine, felodipine, bendroflumethazide, acetazolamide, methazolamide, chlorpropamide, methotrexate, allopurinol, erythromycin, hydrocortisone, triamcinolone, prednisone, prednisolone, norgestrel, norethindone, progesterone, norgesterone, ibuprofen, atenolol, timolol, cimetidine, clonidine, diclofenac, glipizide, lovastatin, fluvastatin, simvastatin, pravastatin, fexofenadine, and the like. Useful water soluble medicaments include various therapeutic agents such as decongestants, antihistamines, analgesics, sedatives, anti-inflammatory, anti-depressants, antihypertensives and the like at therapeutic dosage levels.

Examples of specific medicaments which may be utilized, at therapeutic dose levels, in the controlled release tablets of the invention include ephedrine, pseudoephedrine, phenylpropanolamine, chlorpheniramine, diphenhydramine, dimenhydramine, indomethacin, labetalol, albuterol, haloperidol, amitriptyline, clofenac, clonidine, terfenadine, fentanyl, and the like which are in the form of a water soluble salt such as the hydrochloride or sodium salt or in the from of an ester, ether, amide, complex or the like.

The unitary core osmotic tablet formulation of the invention which contains nifedipine as the medicament has been demonstrated to have bioequivalent pharmacokinetic performance (i.e., maintain a sustained 24 hour drug plasma levels) when compared with multiple layer-preformed aperture tablets which require a complex segmented osmotic core.

In the case of nifedipine, the core of the controlled release tablet of the present invention is preferably made from an amorphous nifedipine which may be formed from crystalline nifedipine which is dissolved in a solvent such as acetone and formed into granules by spraying the solution on an excipient which comprises a water soluble pharmaceutically acceptable polymer binder and a water soluble osmotic agent. In the alternative, crystalline nifedipine may be used.

The medicament, the pharmaceutically acceptable water soluble polymer binder and the water soluble osmotic agent are first formed into a granulation which is subsequently blended with a water swellable osmotic polymer and suitable excipients to form a composition which may be compressed into tablets. In the alternative, the water soluble pharmaceutically acceptable polymer may be combined with the medicament and the water soluble osmotic compound and the water swellable osmotic polymer. After a granulation is formed from this blend, the granules may be tabletted with or without the addition of an additional quantity of a water soluble compound and/or the water swellable osmotic polymer. A tabletting machine is used to compress the granulation mixture into a core tablet having a homogeneous core. The homogeneous core is subsequently completely coated with a modified polymeric membrane to form the controlled release tablet of the invention.

It is believed that as water passes through the membrane on the surface of the tablet of the invention, the core swells and increases the pressure inside the tablet. This causes a very slight expansion of the partially hydrated core which is controlled by the use of a relatively small amount of the water swellable polymer.

The expansion of the core will cause the membrane to open to relieve the internal pressure. Once the initial opening or openings are formed, the swelling effect of the core components will cause the contents of the core to extrude through the initial opening without complete disintegration of the membrane. The internal pressure which is exerted on the membrane by the swelling and expanding osmotic core is relieved by the passage of the first portions of the core contents through the initial openings. This effect is unexpected because it could not have been predicted that small, randomly formed openings in the membrane would form and relieve the internal pressure by gradually controlled release than dose dumping the entire core contents by a bursting or disintegration of the membrane. It is believed that the formation of the small openings, without initial loss of the integrity of the rest of the membrane by uncontrolled expansion of the osmotic core, is responsible for the 24 hour therapeutic blood level which is achieved by the controlled release tablet of the invention.

Figure 2:
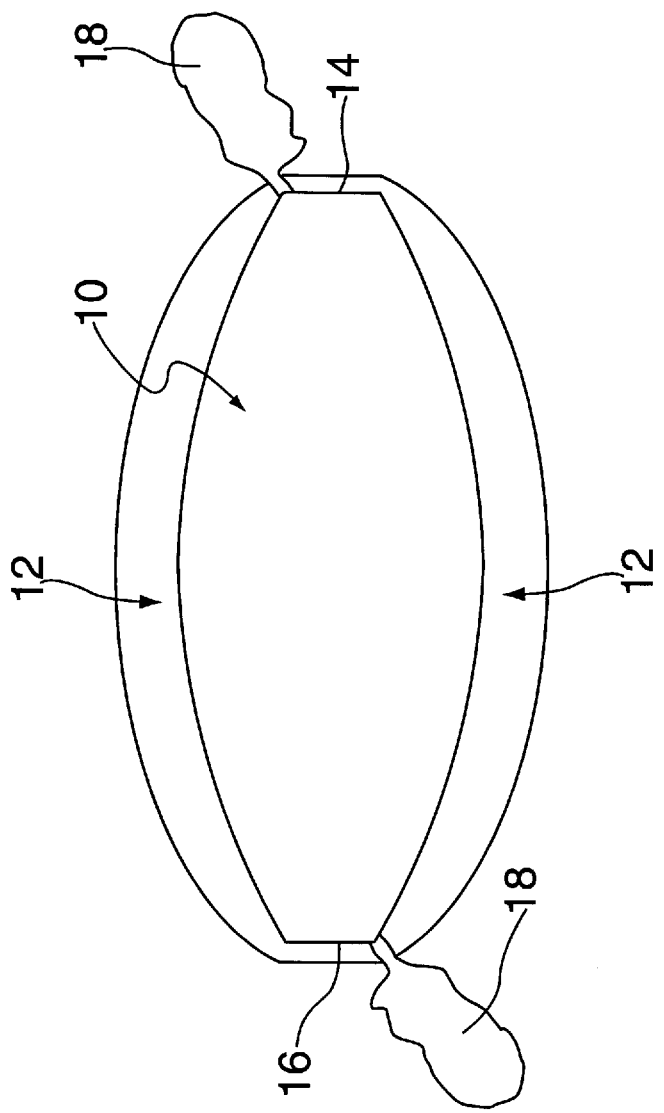
FIG. 2 is a cross-section of a tablet of the invention which shows the extrusion of a portion or portions of the core through a portion of the edge of the tablet which is observed within one hour after a tablet is placed in an aqueous fluid.

FIG. 2 shows a cross-section of a tablet of the invention which illustrates the internal structure of the tablet with core element 10 and membrane 12. The inherent effect of the surface tension results in a relatively thin membrane at edges 14 and 16 is shown by the cross-section. The relatively thin membrane at edges 14 and 16 is typical of the membrane thicknesses obtained when a controlled release coating is applied to any tablet core. The extruding portions of the core 18 which is observed after the tablet is placed in an aqueous fluid appear to resemble an irregularly shaped elastic mass of a portion of the core tablet.

The controlled release tablet of the invention has been used to administer the calcium channel blocker nifedipine.

The preferred water soluble osmotic agents include water soluble organic and inorganic compounds such as sucrose, lactose, dextrose, sodium chloride, sorbic acid, potassium chloride, polyethylene glycol (weight av. molecular weight 380–420), propylene glycol and mixtures thereof. These materials are utilized at a level of 20–60% and preferably from 35–50% based on the weight of the core of the tablet.

The core composition will contain one or more osmotic polymers. If two osmotic polymers are used, one osmotic polymer may be a pharmaceutically acceptable, water soluble polyvinyl pyrrolidone having a weight average molecular weight of 25,000 to 200,000. Other pharmaceutically acceptable water soluble polymers include hydroxy propyl cellulose, hydroxyethylcellulose and the like.

The pharmaceutically acceptable, water soluble osmotic polymer may be employed in an effective amount that will exert an osmotic effect on the release of the calcium channel blocking agent. These amounts will generally be from about 15 to 40%, preferably from about 20 to 30% based on the weight of the compressed tablet core.

The composition of the core also preferably includes as a second osmotic polymer, a pharmaceutically acceptable, water swellable osmotic polymer such as polyethylene oxide having a weight average molecular weight of 100,000 to 6,000,000. Other water swellable osmotic polymers include hydroxypropyl methylcellulose, poly(hydroxy alkyl methacrylate) having a molecular weight of from 30,000 to 5,000,000; poly(vinyl)alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a water insoluble, water swellable copolymer produced by forming a dispersion of a finely divided copolymer of maleic anhydride with styrene, ethylene, propylene, butylene or isobutylene cross-linked with from 0.001 to 0.5 moles of saturated cross-linking agent per mole of maleic anyhydride in the copolymer; Carbopol® acidic carboxy polymers having a molecular weight of 450,000 to 4,000,000; Cyanamer® polyacrylamides; cross-linked water swellable indenemaleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. No. 3,865,108; U.S. Pat. No. 4,002,173 and U.S. Pat. No. 4,207,893 all of which are incorporated by reference. The pharmaceutically acceptable, water swellable polymers may be employed in an effective amount that will control the swelling of the tablet core. These amounts will generally be from about 5 to 15%, preferably from about 7 to 12% based on the weight of the compressed tablet core.

The membrane coating which completely covers said core comprises a water insoluble pharmaceutically acceptable polymer in combination with an enteric polymer. Suitable water insoluble polymers include cellulose esters, cellulose ethers and cellulose ester ethers. These materials include cellulose acylate, cellulose ethyl ether, cellulose diacylate, cellulose triacylate, cellulose acetate, cellulose diacetate, cellulose triacetate, mono-, di- and tricellulose alkyls, mono-, di- and tricellulose aroyls and the like. Cellulose acetate is the preferred polymer. Other water insoluble polymers are disclosed in U.S. Pat. No. 4,765,989 which is incorporated by reference. If desired the above polymer may be combined with from 10 to 40%, preferably 20–30% of an enteric polymer to modify the permeability of the membrane coating around the core. These enteric polymers include Eudragit S (methacrylic acid/methyl methacrylate copolymer with a 1:2 ratio of MA to MMA) or Eudragit L (methacrylic acid/methyl methacrylate copolymer with a 1:1 ratio of MA to MMA), hydroxypropylmethylcellulose phthalate (HPMCP), cellulose acetate phthalate, etc. Generally, the membrane coating around the core will comprise from about 1 to 4% and preferably about 2% based on the total weight of the core tablet.

The water insoluble polymer-enteric polymer mixture may contain an optional plasticizer or a water soluble channeling agent as the modifier. The water soluble channeling agent is a material that dissolves in water to form a porous polymer shell that allows water to be imbibed into the core. This material is used in a sufficient amount to control the lag time for the formation of the initial openings of the coated tablet. These materials include water soluble organic and inorganic compounds such as sucrose, lactose, dextrose, sodium chloride, sorbic acid, potassium chloride, polyethylene glycol (weight av. molecular weight 380–420), propylene glycol and mixtures thereof. The amount of channeling agent may be from 0–50% and preferably from 10–30% based on the total dry weight of the coating composition.

The water insoluble polymer-enteric polymer mixture may be plasticized with a plasticizing amount of a plasticizer. The preferred plasticizer is triacetin but materials such as acetylated monoglyceride, rape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer or water soluble channeling agent, amounts of from 1% to 40%, and preferably 10 to 30% of the modifier based on the total weight of the water insoluble polymer, water soluble polymer and the modifier may be utilized.

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1995 Edition may be used to optimize the formulations of the invention. In the alternative, dry granulation techniques may used to prepare formulation for making compressed tablets.

DESCRIPTION OF THE PREFERRED EMBODIMENTS

EXAMPLE 1

Tablets having the following formula are prepared as follows:

| I Amorphous Granulation | |
|---|---|
| nifedipine (crystalline) | 16.5% |
| povidone[1], USP | 49.5% |
| lactose (anhydrous) | 31.0% |
| sodium lauryl sulfate | 3.0% |
| acetone* (Five times the amount of nifedipine) | |
| isopropyl alcohol* (Five times the amount of nifedipine) | |

[1]weight average molecular weight = 50,000; dynamic viscosity (10% w/v solution at 20° C.) = 5.5–8.5 mPas.
*acetone and isopropyl alcohol are evaporated during the granulation process.

(a) The crystalline nifedipine is first dispersed in acetone and then the povidone is added with stirring until a uniform mixture is formed. The isopropyl alcohol is then added and mixed until a clear solution is formed. The sodium lauryl sulfate is added and the product is continuously stirred until it is used.

(b) The lactose is placed in a fluidized bed dryer to make granules. The solution of the nifedipine, which has been separately prepared in step (a), is sprayed onto the lactose and a granulation containing amorphous nifedipine is obtained. After completion of the granulation step, the drying cycle is initiated. The drying is continued until the moisture loss on drying (LOD) is not more than 2.5%.

| II Tableting | |
|---|---|
| Amorphous granules from (I) | 60.6% |
| lactose(anhydrous) | 24.4% |
| poly(ethyleneoxide)[2], NF | 10.0% |
| glyceryl monostearate[3] | 5.0% |

[2]Polyox ® WSR Coagulent; approximate molecular weight = 5,000,000
[3]Myvaplex 600P (c) A tablet core is made by blending 10.0% of poly (ethyleneoxide), NF; 5.0 wt % of glyceryl monostearate 24.4% lactose; and 60.6% of the granules from step (b), based on the total weight of all ingredients. Core tablets weighing 330 mg each are made in a tablet press machine with 0.3410" standard concave punches and die.

| III Color Coating | |
|---|---|
| Opadry Yellow[4] | 75% |
| sodium chloride | 25% |
| water qs(evaporated during processing) | |

[4]hydroxypropylmethyl cellulose; titanium dioxide; polyethylene glycol 4000 polysorbate 80; D&C yellow No. 10 aluminum lake; and FD&C red #40 aluminum lake (d) The yellow color suspension is applied to the tablets prepared in Step (c) in a perforated coating pan. The coating level is 4% by weight.

The color coating is to protect the drug from light.

| IV  Sustained Release Coating | |
|---|---|
| cellulose acetate (398-3)[5] | 60% |
| Eudragit S100 | 20% |
| triacetin | 5% |
| PEG 400 | 5% |
| sucrose, micronized | 10% |
| acetone qs (evaporated during processing) | |

[5]acetyl content 39.8%)

(e) A sustained release coating is applied to the tablet prepared in Step (d) by coating the tablets in a fluidized-bed coater. The coating level is 2% for this membrane.

A cross-section of a dissolving tablet of Example 1 is shown in FIG. 2. The core 10 is surrounded with membrane 12. At the side (14, 16) of the tablet, the membrane which is formed by coating a liquid onto the compressed tablet core, tends to be thinner than on the larger convex surfaces of the tablet. The opening of the tablet and extruded contents 18 are illustrations of the phenomenon which takes place when the coated tablets of the invention are placed in an aqueous fluid.

EXAMPLE 2

Tablets having the following formula are prepared as follows:

| I  Amorphous Granulation | |
|---|---|
| nifedipine (crystalline) | 10.5% |
| povidone[1], USP | 31.6% |
| lactose (anhydrous) | 45.5% |
| sodium lauryl sulfate | 1.9% |
| poly(ethyleneoxide)[2], NF | 10.5% |
| acetone* (Five times the amount of nifedipine) | |
| isopropyl alcohol* (Five times the amount of nifedipine) | |

[1]weight average molecular weight = 50,000; dynamic viscosity (10% w/v solution at 20° C.) = 5.5–8.5 mPas.
[2]Polyox ® WSR Coagulant; approximate molecular weight = 5,000,000
*acetone and isopropyl alcohol are evaporated during the granulation process.

(a) The crystalline nifedipine is first dispersed in acetone and then the povidone is added with stirring until a uniform mixture is formed. The isopropyl alcohol is then added and mixed until a clear solution is formed. The sodium lauryl sulfate is added and the product is continuously stirred until it is used.

(b) The lactose and the poly(ethylene oxide) are placed in a fluidized bed dryer to make granules. The solution of the nifedipine, which has been separately prepared in step (a), is sprayed onto the lactose mixture and a granulation containing amorphous nifedipine is obtained. After completion of the granulation step, the drying cycle is initiated. The drying is continued until the moisture loss on drying (LOD) is not more than 2.5%.

| II  Tableting | |
|---|---|
| Amorphous granules from (I) | 95.0% |
| glyceryl monostearate[3] | 5.0% |

[3]Myvaplex 600P (c) Core tablets weighing 330 mg each are made in a tablet press machine with 0.3410" standard concave punches and die.

| III  Color Coating | |
|---|---|
| Opadry Yellow[4] | 75% |
| sodium chloride | 25% |
| water qs(evaporated during processing) | |

[4]hydroxypropylmethyl cellulose; titanium dioxide; polyethylene glycol 4000; polysorbate 80; D&C yellow No. 10 aluminum lake; and FD&C red #40 aluminum lake (d) The yellow color suspension is applied to the tablets prepared in Step (c) in a perforated coating pan. The coating level is 4% by weight.

The color coating is to protect the drug from light.

| IV  Sustained Release Coating | |
|---|---|
| cellulose acetate (398-3)[5] | 60% |
| Eudragit S100 | 20% |
| triacetin | 5% |
| PEG 400 | 5% |
| sucrose, micronized | 10% |
| acetone qs (evaporated during processing) | |

[5]acetyl content 39.8%)

(e) A sustained release coating is applied to the tablet prepared in Step (d) by coating the tablets in a fluidized-bed coater. The coating level is 2% for this membrane.

A cross-section of a dissolving tablet of Example 1 is shown in FIG. 2. The core 10 is surrounded with membrane 12.

If desired, the membrane coated tablet may be overcoated with an enteric coating such as the following:

| | |
|---|---|
| hydroxy propyl methyl cellulose phthalate (releases at pH 5.5) | 70% |
| pore forming agent | 0–30% or 5–25% |
| talc, U.S.P. (no pore former) | 23% |
| acetyltributyl citrate (no pore former) | 7% |
| acetone (evaporated during processing) | |

The overcoat is coated onto the membrane coated tablets to add 2 to 5% and preferably about 4.3%

The term "%" as used herein refers to weight percent.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A once a day controlled release tablet which comprises:
(a) a homogeneous compressed core of granules produced in a fluidized bed, said core said core comprising:
(i) a medicament;
(ii) a water soluble osmotic compound;
(iii) one or more osmotic polymers wherein one of the osmotic polymers is a water swellable osmotic polymer; and
(b) a membrane coating which completely covers said core tablet which comprises a mixture of:

(i) a water insoluble pharmaceutically acceptable polymer; and (ii) an enteric polymer.

2. A controlled release pharmaceutical tablet as defined in claim 1 wherein the medicament is a calcium channel blocker compound.

3. A controlled release pharmaceutical tablet as defined in claim 2 wherein the medicament is nifedipine.

4. A controlled release pharmaceutical tablet as defined in claim 1 which includes two osmotic polymers.

5. A controlled release pharmaceutical tablet as defined in claim 1 wherein the water swellable polymer is selected from the group consisting of poly(ethylene oxide), hydroxypropylmethylcellulose and mixtures thereof.

6. A controlled release pharmaceutical tablet as defined in claim 1 wherein the membrane around the core contains an enteric polymer which is a methacrylic acid/methyl methacrylate polymer.

7. A controlled release pharmaceutical tablet as defined in claim 1 wherein the water insoluble polymer in the membrane around the core is a water insoluble cellulose derivative.

8. A controlled release pharmaceutical tablet as defined in claim 7 wherein the water insoluble cellulose derivative in the membrane around the core is cellulose acetate.

9. A controlled release pharmaceutical tablet as defined in claim 1 wherein the mixture of the water insoluble polymer and the enteric polymer contain a plasticizer.

10. A controlled release pharmaceutical tablet as defined in claim 9 wherein the plasticizer is triacetin.

11. A controlled release pharmaceutical tablet as defined in claim 9 wherein the mixture of the water insoluble polymer and the enteric polymer contain a water soluble channeling agent.

12. A controlled release pharmaceutical tablet as defined in claim 9 wherein the mixture of the water insoluble polymer and the enteric polymer is overcoated with an additional layer of an enteric polymer.

13. A controlled release pharmaceutical tablet as defined in claim 12 wherein the enteric polymer overcoat is hydroxypropyl methylcellulose phthalate which is plasticized with acetyltributyl citrate.

14. A once a day controlled release nifedipine tablet which comprises:

(a) a homogeneous compressed core made from granules produced in a fluidized bed process said core consisting essentially of:

(i) nifedipine;

(ii) a water soluble osmotic compound;

(iii) polyethylene oxide; and (b) a membrane coating which completely covers said core tablet which comprises a mixture of:

(i) a water insoluble pharmaceutically acceptable polymer; and (ii) an enteric polymer.

15. A once a day controlled release tablet which comprises:

(a) a homogeneous compressed core of granules produced in a fluidized bed, said core said core consisting essentially of:

(i) a medicament;

(ii) a water soluble osmotic compound;

(iii) one or more osmotic polymers wherein one of the osmotic polymers is a water swellable osmotic polymer; and (b) a membrane coating which completely covers said core tablet which comprises a mixture of:

(i) a water insoluble pharmaceutically acceptable polymer; and (ii) an enteric polymer.

* * * * *